United States Patent
Jung et al.

(10) Patent No.: US 9,588,060 B2
(45) Date of Patent: Mar. 7, 2017

(54) NON-DESTRUCTIVE INSPECTION SYSTEM FOR DISPLAY PANEL AND METHOD, AND NON-DESTRUCTIVE INSPECTION APPARATUS THEREOF

(71) Applicants: Samsung Electronics Co., Ltd., Suwon-si (KR); Oz-tec Co., Ltd, Daegu (KR)

(72) Inventors: Yeong Ri Jung, Yongin-si (KR); Ki Wan Kim, Daegu (KR); Jae Young Kim, Ansan-si (KR)

(73) Assignees: SAMSUNG ELECTRONICS CO., LTD., Suwon-si (KR); OZ-TEC CO., LTD., Daegu (KR)

(*) Notice: Subject to any disclaimer, the term of this patent is extended or adjusted under 35 U.S.C. 154(b) by 82 days.

(21) Appl. No.: 14/540,453

(22) Filed: Nov. 13, 2014

(65) Prior Publication Data
US 2015/0138564 A1 May 21, 2015

(30) Foreign Application Priority Data
Nov. 15, 2013 (KR) .................. 10-2013-0139188

(51) Int. Cl.
*G01B 9/02* (2006.01)
*G01N 21/95* (2006.01)
*G01N 21/88* (2006.01)

(52) U.S. Cl.
CPC ......... *G01N 21/95* (2013.01); *G01B 9/02091* (2013.01); *G01N 21/8806* (2013.01); *G01B 2290/65* (2013.01)

(58) Field of Classification Search
CPC ............ G01B 11/2441; G01B 9/02044; G01B 9/02088; G01J 9/02; G01J 3/2823
(Continued)

(56) References Cited

U.S. PATENT DOCUMENTS 7,417,721 B2 * 8/2008 Uto .................... G01N 21/9501
356/237.2
2009/0213386 A1 * 8/2009 LeBlanc ............ G01B 11/2441
356/495
(Continued)

FOREIGN PATENT DOCUMENTS

EP  1522846 A1  4/2005
JP  2002-341345  11/2002
(Continued)

*Primary Examiner* — Jonathan Hansen
(74) *Attorney, Agent, or Firm* — Staas & Halsey LLP

(57) ABSTRACT

A non-destructive inspection apparatus includes a light source generating light, an optical coupler which divides the light, irradiates the divided light to a reference part and a sample part, generates coherent light, and transmits the coherent light to a detecting part, the reference part which phase-scans the irradiated light and reflects the light, the sample part which irradiates the light incident from the optical coupler to a display panel, and scans and reflects the light reflected from the display panel, the detecting part which obtains an image signal of the display panel from the coherent light, a transferring part which moves a position of the sample part, and the control part which generates an image of the display panel based on the image signal of the display panel transmitted from the detecting part and detects a foreign substance, and controls movement of the transferring part.

23 Claims, 12 Drawing Sheets

(58) Field of Classification Search
USPC .......................... 356/511, 521, 237.3, 239.8
See application file for complete search history.

(56) References Cited

U.S. PATENT DOCUMENTS

2009/0296102 A1* 12/2009 Tamura ................ A61B 5/0066
356/512
2013/0057871 A1  3/2013 Kim et al.

FOREIGN PATENT DOCUMENTS

| JP | 2005-201887 | 7/2005 |
| JP | 2012-159489 | 8/2012 |
| KR | 10-1999-0085258 | 12/1999 |
| KR | 10-2002-0038488 | 5/2002 |
| KR | 10-2005-0035243 | 4/2005 |
| KR | 10-1011575 | 1/2011 |
| KR | 10-2011-0061287 | 6/2011 |
| KR | 10-2013-0078721 | 7/2013 |

* cited by examiner

TWO-DIMENSIONAL TOMOGRAPHIC IMAGE

THREE-DIMENSIONAL RENDERING IMAGE

NON-DESTRUCTIVE INSPECTION SYSTEM FOR DISPLAY PANEL AND METHOD, AND NON-DESTRUCTIVE INSPECTION APPARATUS THEREOF

CROSS-REFERENCE TO RELATED APPLICATIONS

This application claims the priority benefit of Korean Patent Application No. 10-2013-0139188, filed on Nov. 15, 2013 in the Korean Intellectual Property Office, the disclosure of which is incorporated herein by reference.

BACKGROUND

1. Field

The following description relates to a non-destructive inspection system for a display panel and method using a real-time optical tomography technique, and a non-destructive inspection apparatus thereof.

2. Description of the Related Art

Recently, as demand for portable electronic products such as smartphones and tablets has increased, the use of touchscreen panels providing intuitive user interfaces and convenience as input devices such as keyboards has increased. A market for the touchscreen panels is growing rapidly all over the world. Also, various display devices and panels have been gradually developed to have highly multiple and ultra-thin layers, ultra-fine pattern arrays, and integrated chips-packages, and thus, a manufacturing technique thereof has made much progress.

However, in spite of such progress, an inspection method for detecting a defect in an ultra-thin touchscreen panel, or monitoring whole processes and finding a cause of the defect is still reliant on destructive inspection or visual inspection by an operator.

In the past, the inspection could be performed manually. However, in a current touchscreen manufacturing technique similar to a semiconductor manufacturing process, a new method which monitors whole processes in real time and enhances reliability for a complete product is required.

SUMMARY

Therefore, it is an aspect of the present disclosure to provide a non-destructive inspection system for a display panel and method, which non-destructively inspects a defect in producing and manufacturing processes of a touchscreen panel having multiple layers, and the display panel using the same, and a non-destructive inspection apparatus thereof.

Additional aspects of the disclosure will be set forth in part in the description which follows and, in part, will be obvious from the description, or may be learned by practice of the disclosure.

In accordance with an aspect of the present disclosure, a non-destructive inspection apparatus includes a light source generating light, an optical coupler which divides the light generated from the light source, irradiates the divided light to a reference part and a sample part, generates coherent light by combining light reflected and incident from the reference part and the sample part, and transmits the coherent light to a detecting part, the reference part which phase-scans the light incident from the optical coupler at a high speed and then reflects the light, the sample part which irradiates the light incident from the optical coupler to a display panel to be inspected, and scans and reflects the light reflected from the display panel, the detecting part which obtains an image signal of the display panel from the coherent light incident from the optical coupler, a transferring part which moves a position of the sample part up and down according to controlling of a control part so that the display panel is located at a predetermined scan area, and the control part which generates an image of the display panel based on the image signal of the display panel transmitted from the detecting part and detects a foreign substance, and also controls movement of the transferring part.

The sample part may include a first collimating lens which converts incident light into parallel light, a scanner which reflects the parallel light incident from the first collimating lens so that the parallel light is irradiated to a photographing area of the display panel, and a scanning lens which controls focus of the parallel light irradiated through the scanner so that the parallel light is concentrated to one point.

The scanner may control the parallel light output from the first collimating lens in an irradiation direction and may perform scanning in an X-axial direction and a Y-axial direction of the display panel.

The detecting part may obtain a two-dimensional image signal based on a plurality of coherent light beams incident, in turn, according to controlling of the irradiation direction of the parallel light of the scanner.

The scanner may be a galvano-scan mirror.

The control part may generate a one-dimensional cross-sectional display panel image, a two-dimensional tomographic display panel image, and a three-dimensional display panel image based on the image signal transmitted from the detecting part.

The control part may determine whether the foreign substance exists through the one-dimensional cross-sectional display panel image, may determine whether the foreign substance exists between layers and a size of the foreign substance through the two-dimensional tomographic display panel image, and may determine a volume and shape of the foreign substance through the three-dimensional display panel image.

The reference part may include a second collimating lens which converts incident light into parallel light, a first focusing lens which controls focus of the parallel light transmitted through the second collimating lens so that the parallel light is concentrated to one point, and a reference mirror which changes an optical path to reflect the light incident from the first focusing lens.

The detecting part may include a third collimating lens which converts coherent light incident from the optical coupler into parallel light, a diffraction grid which distributes the parallel light according to wavelengths, a second focusing lens which controls focuses of the distributed parallel light so that the distributed parallel light is concentrated to each point according to each wavelength, and a spectrometer which scans the light in a line state incident from the second focusing lens and generates an image signal.

The spectrometer may include a line scan camera comprising a complementary metal-oxide-semiconductor (CMOS) camera and a charge coupled device (CCD) camera.

The non-destructive inspection apparatus may further include a photographing part which is disposed at a position spaced upward from the display panel located on an inspection table to photograph a surface of the display panel and thus primarily detect a foreign substance estimation area on the display panel.

The display panel may be a touchscreen panel or a display device to which the touchscreen panel is applied.

In accordance with an aspect of the present disclosure, a non-destructive inspection system which is connected with a non-destructive inspection apparatus to detect a foreign substance in a display panel includes an image signal processing part which generates an image of the display panel from an image signal of an electrical signal type transmitted from the non-destructive inspection apparatus, a foreign substance detecting part which determines existence of the foreign substance by comparing the image of the display panel with a previously stored reference image, calculates a size of the determined foreign substance, compares the calculated size with a predetermined reference size of the foreign substance, and thereby determines a defect is present when the calculated size exceeds the predetermined reference size of the foreign substance, and a displaying part which displays a real-time monitoring state of the display panel generated from the image signal processing part.

The non-destructive inspection apparatus may include a sample part for irradiating light to the display panel and a transferring part which moves a position of the sample part up and down, and the non-destructive inspection system may further include a focusing control part which compares brightness of a particular area of the image of the display panel, which is obtained by scanning the display panel using the sample part, with reference brightness, and controls an up and down position of the sample part through the transferring part according to comparison results.

The focusing control part may fix the sample part to a present position, when the brightness of the particular area of the image of the display panel exceeds the reference brightness, and may move the position of the sample part up and down when the brightness of the particular area of the image of the display panel is less than or equal to the reference brightness.

The image signal processing part may include an A/D converter which converts an analog type image signal output from the non-destructive inspection apparatus into a digital type image signal, and an image generating part which generates a display panel image based on the digital type image signal, generates a one-dimensional cross-sectional display panel image and a two-dimensional tomographic display panel image based on the digital signal, and generates a three-dimensional display panel image for each layer of the display panel based on the two-dimensional tomographic display panel image.

The foreign substance detecting part may include a foreign substance size calculating part which detects the foreign substance by comparing the image of the display panel with a previously stored reference image and calculates a size of the foreign substance through location coordinates of the foreign substance from the image of the display panel, and a foreign substance deciding part which decides a defect when the size of the foreign substance calculated through the foreign substance detecting part exceeds the predetermined reference size of the foreign substance.

The display panel may be a touchscreen panel or a display device to which the touchscreen panel is applied.

In accordance with an aspect of the present disclosure, a non-destructive inspection method may include dividing light emitted from a light source and irradiating the divided light to a reference part and a sample part through a non-destructive inspection apparatus, phase-scanning light incident from an optical coupler at a high speed and then reflecting the light through the reference part, irradiating light incident from the optical coupler to a display panel to be inspected, and scanning and reflecting the light reflected from the display panel through the sample part, generating a one-dimensional display panel image based on light incident from the reference part and the sample part, generating a two-dimensional display panel image based on image signals obtained in turn, and generating a three-dimensional display panel image based on the two-dimensional display panel image.

The non-destructive inspection method may further include primarily determining a foreign substance estimation area located on a surface of the display panel, before the dividing of light and the irradiating of the divided light to the reference part and the sample part.

In the irradiating of light to a display panel to be inspected, and the scanning and reflecting of the light reflected from the display panel, when irradiating the light to the display panel, the light may be irradiated along a predetermined observation range on the basis of the foreign substance estimation area.

When the light is irradiated along the predetermined observation range, the light may be irradiated to a single point.

The non-destructive inspection method may further include calculating a size of a foreign substance from the two-dimensional display panel image, and deciding a defect when the calculated size of the foreign substance exceeds a predetermined size of the foreign substance, after the generating of a three-dimensional display panel image.

The non-destructive inspection method may further include moving the sample part up and down so that the display panel to be inspected is located at a predetermined scan area before the dividing of light and the irradiating of the divided light to the reference part and the sample part.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
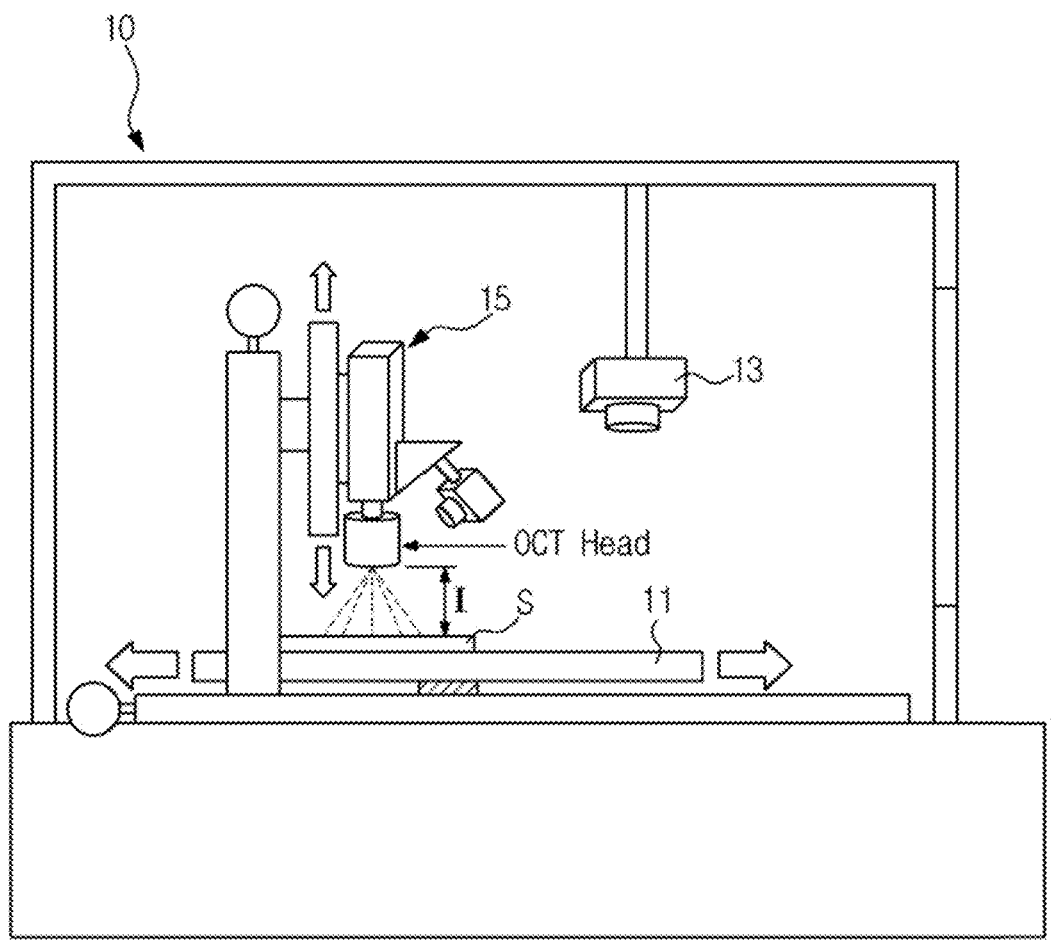
FIG. 1 is a view illustrating an external appearance of a non-destructive inspection apparatus.

Reference will now be made in detail to the embodiments, examples of which are illustrated in the accompanying drawings, wherein like reference numerals refer to like elements throughout. The embodiments are described below to explain the present disclosure by referring to the figures.

Objects, particular advantages, and novel characteristics of the present disclosure will be more apparent from the following detailed description and preferred embodiments in connection with the accompanying drawings. In the drawings, the same components are designated by the same reference numerals, even though they are depicted in different drawings. In the following description, if it is considered that the specific description of the related and noticed functions or structures may obscure the gist of the present disclosure, the specific description will be omitted. Furthermore, the terms first, second, and the like in the description and in the claims are used for distinguishing one component from other components, and thus the components should not be limited by the terms.

Embodiments of the present disclosure will be described herein below with reference to the accompanying drawings.

FIG. 1 is a view illustrating an external appearance of a non-destructive inspection apparatus.

As illustrated in FIG. 1, a non-destructive inspection apparatus 10 may include an inspection table 11 on which a display panel S to be inspected is located, a photographing part 13 which photographs a surface of the display panel S and primarily detects a foreign substance estimation area, and an optical coherence tomography (OCT) device 15 which obtains a one-dimensional cross-sectional display panel image, a two-dimensional tomographic display panel image, and a three-dimensional rendering display panel image of the display panel S through an optical tomography technique, and detects foreign substances. The foreign substance estimation area refers to an estimated area in which it is estimated that the foreign substances exist. The foreign substance estimation area may be detected through the obtained images.

Also, the OCT device 15 may determine a size of each of the foreign substances, a position of a corresponding layer on which the foreign substances exist, and a volume of each of the foreign substances, as well as whether the foreign substances exist through the obtained one-dimensional, two-dimensional, and three-dimensional images. Also, the display panel to be inspected may be a touchscreen panel having multiple layers, or a display device to which the touchscreen panel is applied, such as a mobile phone, a personal digital assistant (PDA), a portable multimedia player (PMP), or a laptop, for example. The display panel is not limited thereto and may include home appliances, such as a television or a refrigerator, for example, which have a multilayered structure like in the touchscreen panel, or to which the touchscreen panel is applied. The display panel may include a flexible display.

The non-destructive inspection apparatus 10 as described above determines a defect generated by foreign substances, such as air bubbles or fine dust, for example, in a touchscreen panel manufacturing process or a display panel manufacturing process, including a process of bonding the touchscreen panel to the display panel S, using the one-dimensional, two-dimensional, and three-dimensional images obtained in real time.

Figure 2:
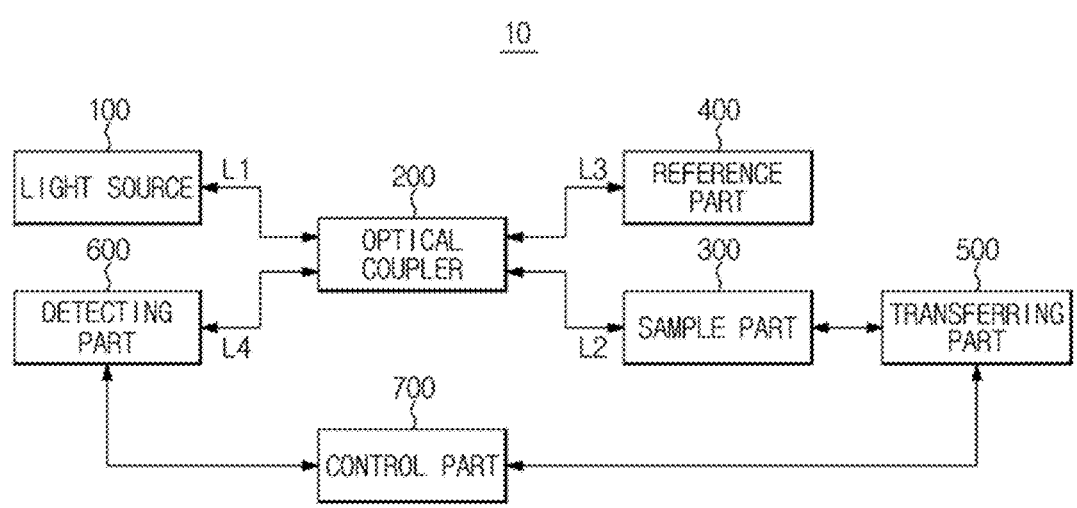
FIG. 2 is a block diagram illustrating a configuration of the non-destructive inspection apparatus.
Figure 3:
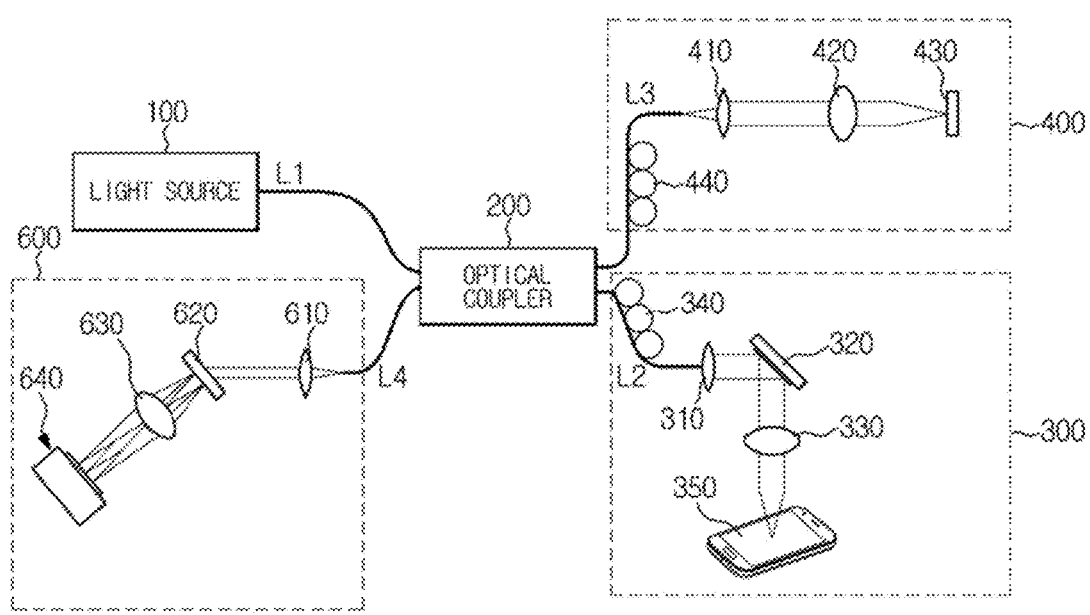
FIG. 3 is a detailed view illustrating a partial configuration of the non-destructive inspection apparatus.

FIG. 2 is a block diagram illustrating a configuration of the non-destructive inspection apparatus, and FIG. 3 is a detailed view illustrating a partial configuration of the non-destructive inspection apparatus.

Figure 9:
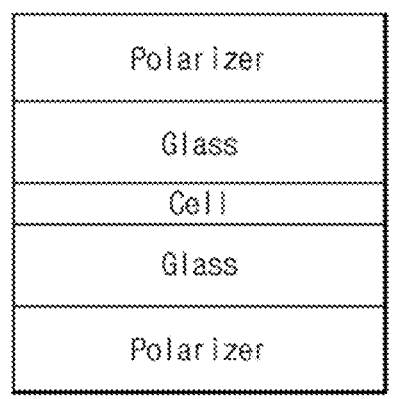
FIG. 9 is a view illustrating a structure of a touchscreen panel to be inspected.
Figure 10:
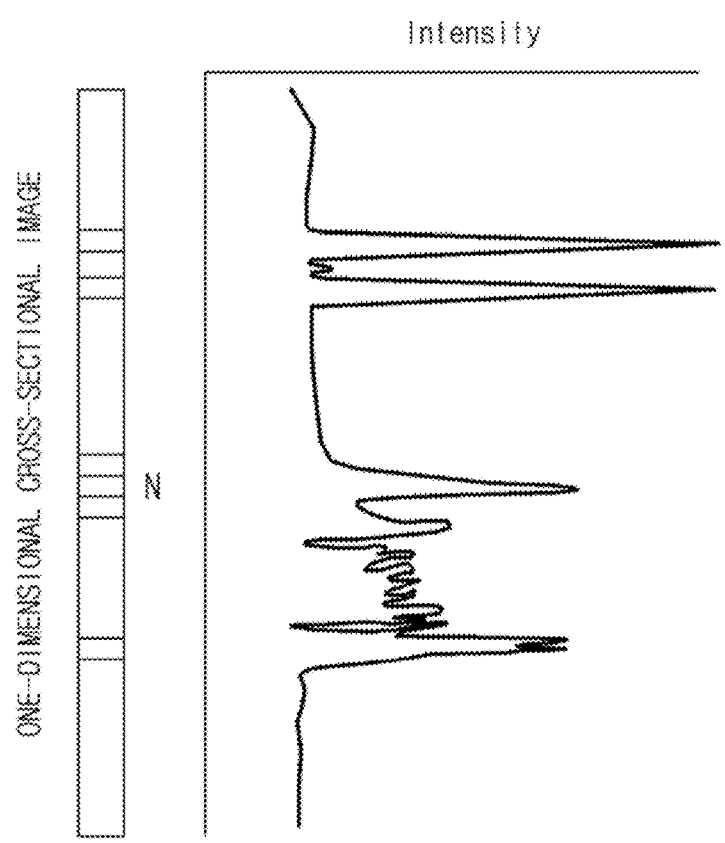
FIG. 10 is a view illustrating an example of a one-dimensional cross-sectional image obtained through a non-destructive inspection.
Figure 11:
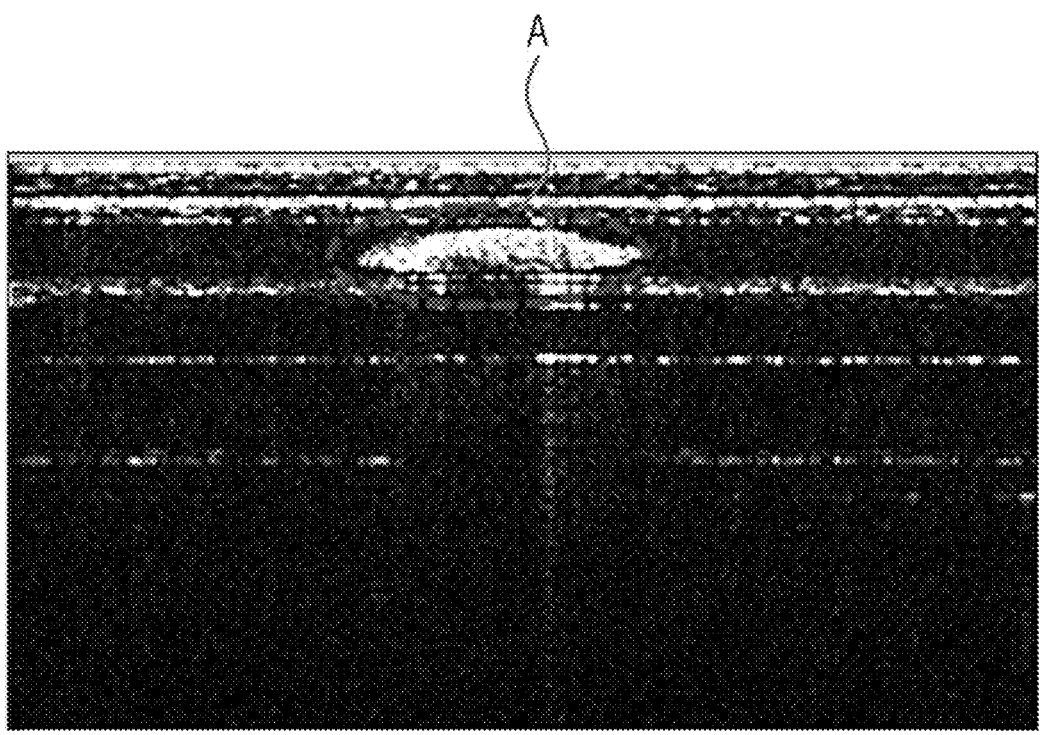
FIG. 11 is a view illustrating an example of a two-dimensional tomographic image obtained through a non-destructive inspection.
Figure 12:
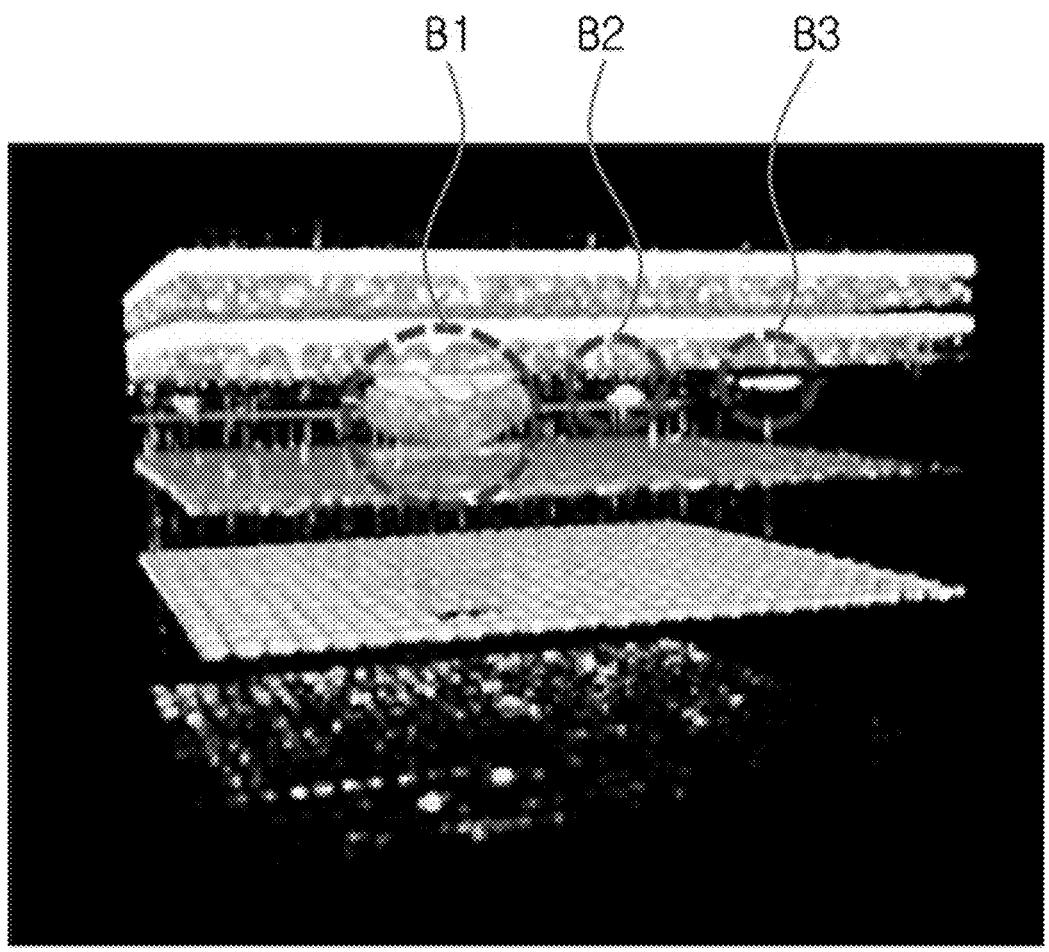
FIG. 12 is a view illustrating an example of a three-dimensional rendering image obtained through a non-destructive inspection.

Hereinafter, description will be provided with reference to FIG. 9 illustrating a structure of the touchscreen panel to be inspected, FIG. 10 illustrating an example of the one-dimensional cross-sectional image obtained through a non-destructive inspection, FIG. 11 illustrating an example of the two-dimensional tomographic image obtained through a non-destructive inspection, and FIG. 12 illustrating an example of the three-dimensional rendering image obtained through a non-destructive inspection.

As illustrated in FIG. 2, the non-destructive inspection apparatus 10 may include a light source 100 generating light, an optical coupler 200, a sample part 300, a reference part 400, a transferring part 500, a detecting part 600, and a control part 700. The light source 100, the sample part 300, the reference part 400, the transferring part 500, and the detecting part 600 may be embodied in the OCT device 15, but the disclosure is not limited thereto.

More specifically, the optical coupler 200 may divide light L1 generated from the light source 100 into light L2 and light L3, may output the divided light to the reference part 400 and the sample part 300, may generate coherent light L4 by combining the light L2 and light L3 reflected and incident from the reference part 400 and the sample part 300, and then may transmit the coherent light L4 to the detecting part 600. The optical coupler 200 may divide a broadband source in a ratio of 50:50, but the disclosure is not limited thereto.

The sample part 300 may irradiate the light L2 incident from the optical coupler 200 to a display panel (350 of FIG. 3) to be inspected and may scan and reflect the light reflected from the display panel 350. The display panel 350 may be a touchscreen panel having multiple layers (e.g., a touchscreen panel having multiple layers in the order of polarizer/glass/cell/glass/polarizer of FIG. 9) or a display device to which the touchscreen panel is applied. However, the display panel 350 is not limited thereto and may include home appliances, such as a television or a refrigerator, for example, to which the touchscreen panel is applied.

As illustrated in FIG. 3, the sample part 300 may include a first collimating lens 310 converting incident light into parallel light, a scanner 320 reflecting the parallel light incident from the first collimating lens 310 so that the parallel light is irradiated to a photographing area of the display panel 350, and a scanning lens 330 controlling focus of the parallel light irradiated through the scanner 320 so that the parallel light is concentrated to one point. The sample part 300 may further include a polarization controller 340 which is disposed between the optical coupler 200 and the first collimating lens 310 to output polarized light. Also, the scanner may be a galvano-scan mirror.

That is, the sample part 300 converts the light output from the optical coupler 200 into the parallel light through the first collimating lens 310 and then irradiates the light beam concentrated through the scanner 320 and the scanning lens 330 to the display panel 350 to be inspected. And reflected light back-scattered by a scatterer of the display panel 350 is incident again to the optical coupler 200 through the scanning lens 330, the scanner 320, and the first collimating lens 310.

The scanner 320 may control the parallel light output from the first collimating lens 310 in an irradiation direction and thus may perform scanning in an X-axial direction (a transverse direction) and a Y-axial direction (a longitudinal direction) of the display panel 350. Therefore, the detecting part 600 may obtain a two-dimensional image signal based on a plurality of coherent light beams incident, in turn, according to controlling of the irradiation direction of the parallel light of the scanner 320. That is, it is possible to obtain a two-dimensional tomographic display panel image through connection of the plurality of coherent light beams obtained, in turn, while the scanner 320 is moved. A three-dimensional image signal is obtained based on the obtained two-dimensional image signal.

The reference part 400 may phase-scan the light L3 incident from the optical coupler 200 at a high speed and then may reflect the light L3.

As illustrated in FIG. 3, the reference part 400 may include a second collimating lens 410 converting incident light into parallel light, a first focusing lens 420 controlling focus of the parallel light transmitted through the second collimating lens 410 so that the parallel light is concentrated to one point, and a reference mirror 430 changing an optical path to reflect the light incident from the first focusing lens 420. The reference part 400 may further include a polarization controller 440 which is disposed between the optical coupler 200 and the second collimating lens 410 to output polarized light.

The detecting part 600 may obtain an image signal of the display panel 350 from the coherent light L3 incident from the optical coupler 200. The detecting part 600 may include a photographing device having an OCT function. Therefore, the detecting part 600 may obtain pixel information on pixels of the photographing device. The pixel information may be used in determining a size of the foreign substance from an image of the display panel.

As illustrated in FIG. 3, the detecting part 600 may include a third collimating lens 610 converting the coherent light L4 incident from the optical coupler 200 into parallel light, a diffraction grid 620 distributing the parallel light according to wavelengths, a second focusing lens 630 controlling focuses of the distributed parallel light so that the distributed parallel light is concentrated to each point according to each wavelength, and a spectrometer 640 scanning the light in a line state incident from the second focusing lens 630 and generating an image signal.

The spectrometer 640 may include a line scan camera including a complementary metal-oxide-semiconductor (CMOS) camera and a charge coupled device (CCD) camera.

The transferring part 500 may move a position of the sample part 300 up and down according to controlling of the control part 700 so that the display panel 350 is located at a predetermined scan area. Referring to FIG. 1, the transferring part 500 adjusts a distance I between the display panel (S of FIG. 1) located on the inspection table 11 (FIG. 1) and a head portion (an OCT head) of the sample part 300 according to the controlling of the control part 700 and enables automatic focusing. Accordingly, because a series of operations relevant to the inspection of the foreign substances in the display panel may be performed automatically and the focusing for obtaining an image may be performed more precisely, it is possible to enhance reliability for inspection results of the foreign substances in the display panel.

The control part 700 may generate an image of the display panel 350 based on the image signal of the display panel 350 transmitted from the detecting part 600 and may detect the foreign substances, and also may control movement of the transferring part 500. However, the control part 700 is not limited thereto and may control other operations of the non-destructive inspection apparatus 10.

More specifically, the control part 700 may generate a one-dimensional cross-sectional display panel image (referring to FIG. 10), a two-dimensional tomographic display panel image (referring to FIG. 11) and a three-dimensional display panel image (referring to FIG. 12) based on the image signal transmitted from the detecting part 600. The two-dimensional tomographic display panel image may be obtained through the coherent light obtained by that the scanner 320 of the sample part 300 irradiates the light to the display panel 350 while controlling the irradiation direction and then scans, in turn, the light reflected from the display panel 350.

For example, as illustrated in FIG. 9, because the touchscreen panel and the display panel to which the touchscreen panel is applied have multiple layers (polarizer/glass/cell/glass/polarizer) of which each is made of a different material, different refractive indexes N may appear on a one-dimensional cross-section, as illustrated in FIG. 10. Also, intensity of the touchscreen panel and an ultraviolet adhesive may also appear differently. Due to this principle, if an area in an object to be inspected, which exceeds a standard value of a refractive index according to each material, is found, it may be determined that a foreign substance exists.

Also, the control part 700 may determine whether the foreign substance exists through the one-dimensional cross-sectional display panel image, may determine whether the foreign substance A (FIG. 11) exists between layers and a size of the foreign substance through the two-dimensional tomographic display panel image, and may determine each volume and shape of the foreign substances B1, B2, and B3 (FIG. 12) through the three-dimensional display panel image. In the two-dimensional tomographic display panel image according to the present disclosure, the foreign substance may be displayed as A of FIG. 11, and in the three-dimensional display panel image, each shape of the foreign substances may be displayed as B1, B2, and B3 of FIG. 12.

As illustrated in FIG. 1, the non-destructive inspection apparatus 10 may further include the photographing part 13 which is disposed at a position above the display panel S located on the inspection table 11 to photograph the surface of the display panel S and thus primarily detect the foreign substance estimation area on the display panel S. Therefore, when the sample part 300 irradiates the light to the display panel 350, the light may be irradiated along a predetermined observation range on the basis of the foreign substance estimation area. At this time, when the light is irradiated along the predetermined observation range, the light may be irradiated to a single point.

Figure 4:
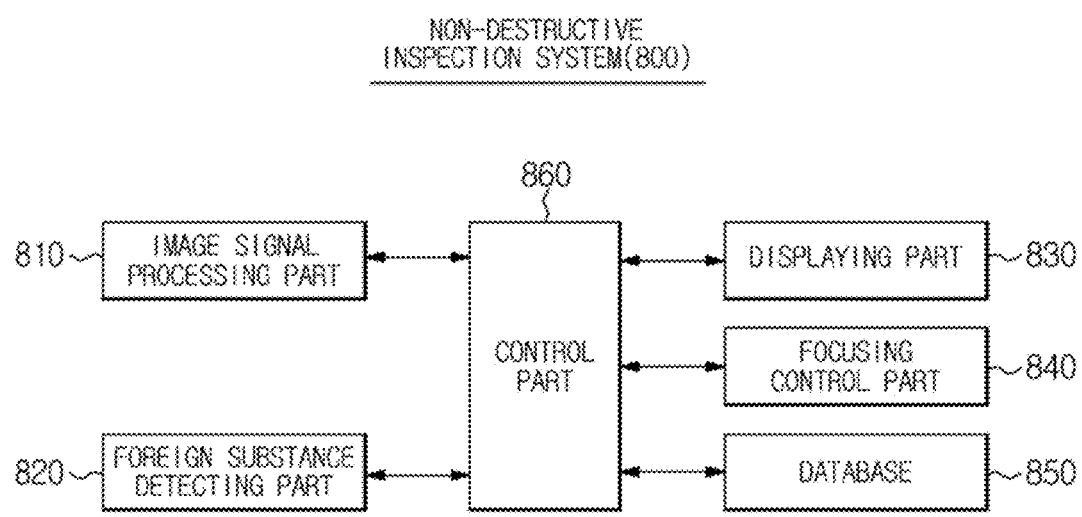
FIG. 4 is a view illustrating a configuration of a non-destructive inspection system.
Figure 5:
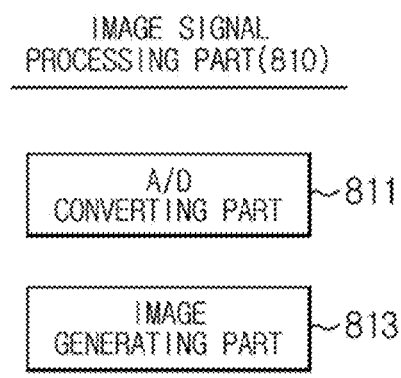
FIG. 5 is a view illustrating a configuration of an image signal processing part.
Figure 6:
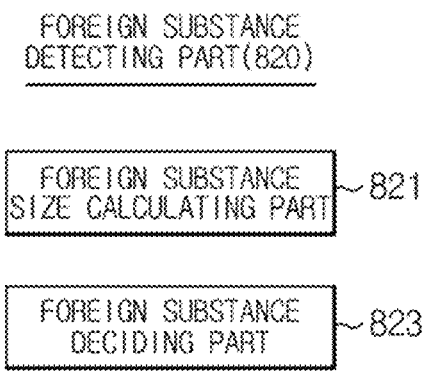
FIG. 6 is a view illustrating a configuration of a foreign substance detecting part.

FIG. 4 is a view illustrating a configuration of a non-destructive inspection system, FIG. 5 is a view illustrating a configuration of an image signal processing part, and FIG. 6 is a view illustrating a configuration of a foreign substance detecting part. Hereinafter, a non-destructive inspection system 800 in which the control part 700 of FIG. 2 is described more specifically will be described with reference to the drawings.

As illustrated in FIG. 4, the non-destructive inspection system 800 which is connected with the non-destructive inspection apparatus to detect the foreign substance in the display panel may include an image signal processing part 810, a foreign substance detecting part 820, a displaying part 830, a focusing control part 840, a database 850, and a control part 860.

More specifically, the image signal processing part 810 may generate the image of the display panel from an image signal of an electrical signal type transmitted from the non-destructive inspection apparatus 10. The display panel (350 of FIG. 3) may be a touchscreen panel or a display device to which the touchscreen panel is applied.

As illustrated in FIG. 5, the image signal processing part 810 may include an A/D converting part 811 which converts an analog type image signal output from the non-destructive inspection apparatus 10 into a digital type image signal, and an image generating part 813 which generates a display panel image based on the digital type image signal, generates the one-dimensional cross-sectional display panel image and the two-dimensional tomographic display panel image based on the digital signal, and generates the three-dimensional display panel image for each layer of the display panel based on the two-dimensional tomographic display panel image.

The foreign substance detecting part 820 may determine the existence of the foreign substance by comparing the image of the display panel with a previously stored reference image, may calculate a size of the determined foreign substance, may compare the calculated size with a predetermined reference size of the foreign substance, and thereby may determine a defect is present when the calculated size exceeds the predetermined reference size of the foreign substance.

As illustrated in FIG. 6, the foreign substance detecting part 820 may include a foreign substance size calculating part 821 which detects the foreign substance by comparing the image of the display panel with the previously stored reference image and calculates the size of the foreign substance through location coordinates of the foreign substance from the image of the display panel, and a foreign substance deciding part 823 which determines a defect is present when the size of the foreign substance calculated through the foreign substance size calculating part 821 exceeds the predetermined reference size of the foreign substance.

The displaying part 830 may display a real-time monitoring state of the display panel generated from the image signal processing part 810.

The focusing control part 840 may compare a brightness of a particular area of the display panel image, which is obtained by scanning the display panel 350 using the sample part 300 (FIG. 2), with a reference brightness, and may control an up and down position of the sample part 300 through the transferring part 500 (FIG. 2) according to the comparison results.

When the brightness of the particular area of the display panel image exceeds the reference brightness, the focusing control part 840 may fix the sample part 300 to a present position, and when the brightness of the particular area of the display panel image is less than or equal to the reference brightness, the focusing control part 840 may move the position of the sample part 300 up and down. That is, the focusing control part 840 controls a distance between the display panel 350 and the OCT head (referring to FIG. 1) of the sample part 300, which irradiates light to the display panel 350, in order to obtain a high quality display panel image.

Figure 7:
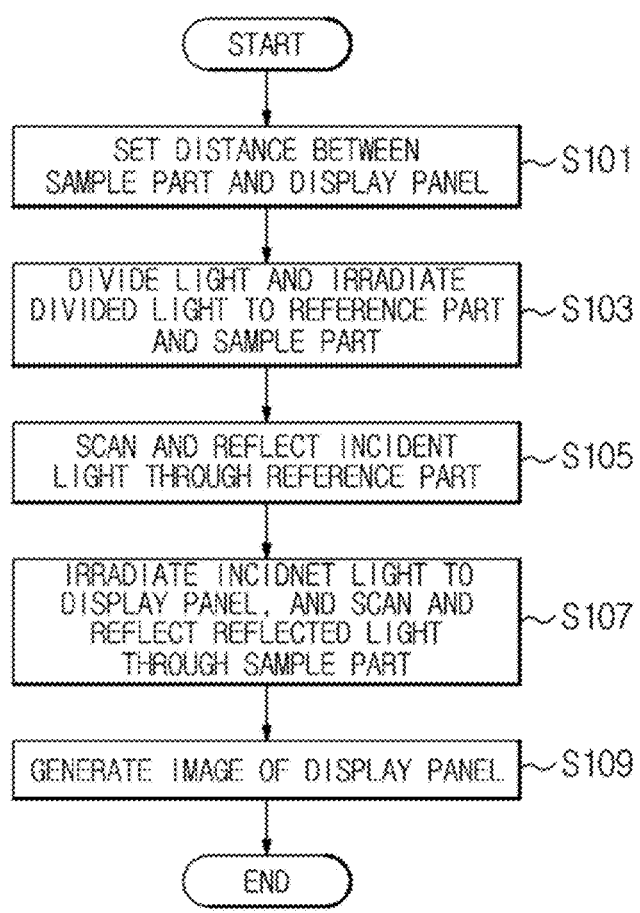
FIGS. 7 and 8 are flowcharts illustrating a non-destructive inspection method.
Figure 8:
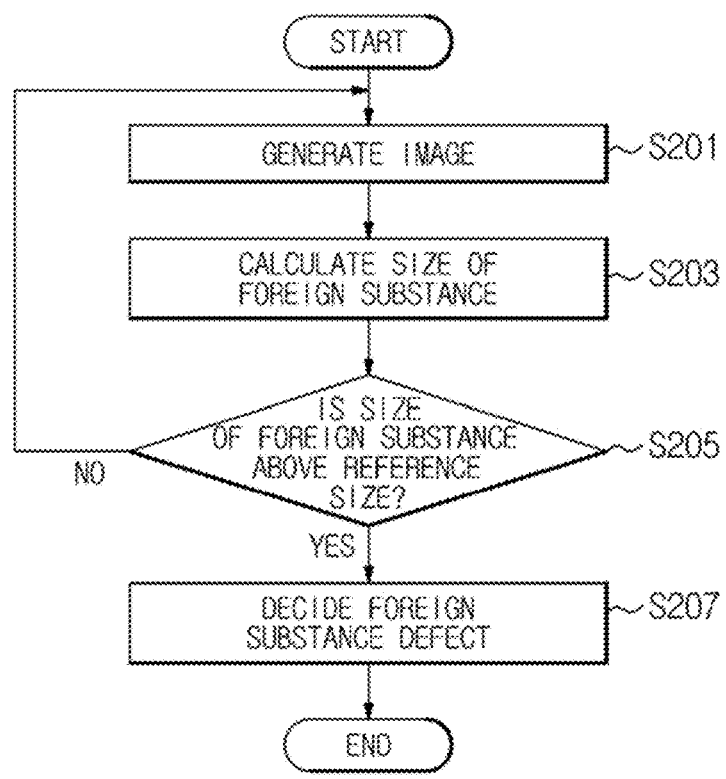

FIGS. 7 and 8 are flowcharts illustrating a non-destructive inspection method.

As illustrated in FIG. 7, the non-destructive inspection apparatus 10 may move the sample part 300 up and down so that the display panel 350 to be inspected is located at the predetermined scan area (operation S101).

More specifically, the non-destructive inspection apparatus 10 may set an initial distance between the sample part 300 and the display panel 350 located on the inspection table 11, may scan the display panel 350 through the sample part 300, and thus may obtain the display panel image. The non-destructive inspection apparatus 10 may compare the brightness of the particular area of the display panel image with the reference brightness, fix the sample part 300 to the present position when the brightness of the particular area of the display panel image exceeds the reference brightness, and move the position of the sample part 300 up or down when the brightness of the particular area of the display panel image is less than or equal to the reference brightness.

The non-destructive inspection apparatus 10 may divide the light emitted from the light source 100 and then may output to the reference part 400 and the sample part 300 (operation S103).

The reference part 400 may phase-scan the light incident from the optical coupler 200 at a high speed and reflect the light (operation S105).

The sample part 300 may irradiate the light incident from the optical coupler 200 to the display panel 350 to be inspected, scan the light reflected from the display panel 350 to be inspected, and reflect the light (operation S107).

The operation S105 and the operation S107 may be performed at the same time, or the operation S107 may be performed before the operation S105.

The display panel image may be generated based on the light incident from the reference part 400 and the sample part 300 (operation S109).

In the operation S109, the non-destructive inspection apparatus 10 may generate the one-dimensional display panel image based on the light incident from the reference part 400 and the sample part 300, may generate the two-dimensional display panel image based on the image signal obtained in turn, and may generate the three-dimensional display panel image based on the two-dimensional display panel image.

Meanwhile, although not shown, before the operation S103 of dividing the light and then irradiating the divided light to the reference part and the sample part, the non-destructive inspection apparatus 10 may primarily determine the foreign substance estimation area on the surface of the display panel 350 through the photographing part 13 (FIG. 1).

Therefore, in the operation S107, when irradiating the light to the display panel 350, the light may be irradiated along a predetermined observation range on the basis of the foreign substance estimation area. At this time, when the light is irradiated along the predetermined observation range, the light may be irradiated to a single point. By concentrically performing the foreign substance inspection within the predetermined observation range on the basis of the foreign substance estimation area, it is possible to rapidly and precisely perform the foreign substance inspection, compared to a case of irradiating the light over an entire surface of an object to be inspected.

Operations in the flowchart of FIG. 8 may be carried out after the operation S109.

As in operation S109, the display panel image may be generated based on the light incident from the reference part 400 and the sample part 300 (operation S201).

The non-destructive inspection apparatus 10 may calculate the size of the foreign substance from the two-dimensional display panel image (operation S203).

More specifically, the non-destructive inspection apparatus 10 detects the foreign substance by comparing the display panel image with the previously stored reference image and calculates the size of the foreign substance through the location coordinates of the foreign substance.

the non-destructive inspection apparatus 10 checks whether the calculated size of the foreign substance exceeds the predetermined size of the foreign substance (operation S205), and it is possible to determine whether a defect is present, when the calculated size of the foreign substance exceeds the predetermined size of the foreign substance (operation S207).

Because the method of inspecting the defect of the display panel using the non-destructive inspection apparatus may determine a corresponding layer on which the foreign substance exists as well as whether the foreign substance exists in each layer of the display panel, through the two-dimensional and three-dimensional images, and may also determine the size and volume of the foreign substance, it is possible to enhance reliability for the inspection results, compared to the conventional method of inspecting only a surface of a product. Also, because it is possible to determine the layer on which the foreign substance exists, only the corresponding layer may be replaced when the defect is found, and thus it is possible to improve productivity and reduce production costs, compared to a conventional case in which an entire defective product may be scrapped.

In accordance with an aspect of the non-destructive inspection system for the display panel and method, and the non-destructive inspection apparatus thereof, because the size and position of the foreign substance may be non-destructively provided in real time, it is possible to secure efficiency and reliability in the manufacturing process.

Also, because the display panel is inspected using the real-time OCT technique, it is possible to determine detailed information of the foreign substance, such as the size and volume of the foreign substance and whether the foreign substance exists between layers, through the one-dimensional, two-dimensional, and three-dimensional images, when the defect occurs.

The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A non-destructive inspection apparatus comprising:
   a light source generating light;
   an optical coupler which divides the generated light, irradiates the divided light to a reference part and a sample part, generates coherent light by combining light reflected and incident from the reference part and the sample part, and transmits the coherent light to a detecting part;
   the reference part which phase-scans the light incident from the optical coupler and includes a reference mirror to reflect the light;
   the sample part which irradiates the light incident from the optical coupler to a display panel, and includes a scanner to scan and reflect the light reflected from the display panel;
   the detecting part including a spectrometer to obtain an image signal of the display panel from the coherent light incident from the optical coupler;
   a transferring device which moves a position of the sample part up and down according to the scanning of the light reflected from the display panel by the sample part so that the display panel is located at a predetermined scan area, thereby enabling automatic focusing on the display panel to be inspected; and
   a controller comprising at least one processor configured to:
   generate a one-dimensional cross-sectional display panel image, a two-dimensional tomographic display panel image, and a three-dimensional display panel image based on the image signal transmitted from the detecting part, and identify existence of a foreign substance based on a refractive index according to each material appearing on the one-dimensional cross-sectional display panel image,
   generate an image of the display panel based on the image signal of the display panel transmitted from the detecting part and detect a foreign substance, and
   control movement of the transferring device according to the scanning of the light reflected from the display panel by the sample part.

2. The apparatus according to claim 1, wherein:
   the sample part further includes a first collimating lens and a scanning lens;
   the first collimating lens converts the incident light from the optical coupler into parallel light;
   the scanner reflects the parallel light incident from the first collimating lens so that the parallel light is irradiated to a photographing area of the display panel; and
   the scanning lens controls focus of the parallel light irradiated through the scanner so that the parallel light is concentrated to one point.

3. The apparatus according to claim 2, wherein the scanner controls the parallel light output from the first collimating lens in an irradiation direction and performs scanning in an X-axial direction and a Y-axial direction of the display panel.

4. The apparatus according to claim 3, wherein the detecting part obtains a two-dimensional image signal based on a plurality of coherent light beams incident, in turn, according to controlling of the irradiation direction of the parallel light of the scanner.

5. The apparatus according to claim 2, wherein the scanner is a galvano-scan mirror.

6. The apparatus according to claim 1, wherein the controller determines whether the foreign substance exists through the one-dimensional cross-sectional display panel image, determines whether the foreign substance exists between layers and a size of the foreign substance through the two-dimensional tomographic display panel image, and determines a volume and shape of the foreign substance through the three-dimensional display panel image.

7. The apparatus according to claim 1, wherein:
the reference part further includes a second collimating lens and a first focusing lens;
the second collimating lens converts incident light into parallel light;
the first focusing lens controls focus of the parallel light transmitted through the second collimating lens so that the parallel light is concentrated to one point; and
the reference mirror changes an optical path to reflect the light incident from the first focusing lens.

8. The apparatus according to claim 1, wherein:
the detecting part further includes a third collimating lens, a diffraction grid and a second focusing lens;
the third collimating lens converts coherent light incident from the optical coupler into parallel light;
the diffraction grid distributes the parallel light according to wavelengths;
the second focusing lens controls focuses of the distributed parallel light so that the distributed parallel light is concentrated to each point according to each wavelength; and
the spectrometer scans the light in a line state incident from the second focusing lens and generates an image signal.

9. The apparatus according to claim 1, wherein the spectrometer comprises a line scan camera comprising a complementary metal-oxide-semiconductor (CMOS) camera and a charge coupled device (CCD) camera.

10. The apparatus according to claim 1, further comprising a photographing part which is disposed at a position above the display panel located on an inspection table to photograph a surface of the display panel and detect a foreign substance estimation area on the display panel.

11. The apparatus according to claim 1, wherein the display panel to be inspected is a touchscreen panel or a display device to which the touchscreen panel is applied.

12. A non-destructive inspection system, which is connectable to the non-destructive inspection apparatus recited in claim 1, to store a reference image and a predetermined reference size and to detect a foreign substance in a display panel, the non-destructive inspection system comprising:
an image signal processing part in conjunction with the controller, which generates an image of the display panel from an image signal of an electrical signal type transmitted from the non-destructive inspection apparatus;
a foreign substance detecting part in conjunction with the controller, which determines an existence of the foreign substance by comparing the image of the display panel with the previously stored reference image, calculates a size of the determined foreign substance, compares the calculated size with the predetermined reference size of the foreign substance, and determines that a defect is present when the calculated size exceeds the predetermined reference size of the foreign substance; and
a displaying part in conjunction with the controller, which displays a real-time monitoring state of the display panel generated from the image signal processing part,
wherein the image signal processing part, the foreign substance detecting part and the displaying part are implemented by at least one processor that executes instructions stored in at least one memory.

13. The system according to claim 12, wherein the non-destructive inspection apparatus comprises: a focusing controller in conjunction with the controller, which compares a brightness of a particular area of the image of the display panel, which is obtained by scanning the display panel using the sample part, with a reference brightness, and controls an up and down position of the sample part through the transferring device according to comparison results,
wherein the focusing controller is implemented by at least one processor that executes instructions stored in at least one memory.

14. The system according to claim 13, wherein the focusing controller:
fixes the sample part to a present position, when the brightness of the particular area of the image of the display panel exceeds the reference brightness, and
moves the position of the sample part up and down when the brightness of the particular area of the image of the display panel is less than or equal to the reference brightness.

15. The system according to claim 12, wherein the image signal processing part comprises:
an A/D converting part which converts an analog type image signal output from the non-destructive inspection apparatus into a digital type image signal; and
an image generating part which generates a display panel image based on the digital type image signal, generates a one-dimensional cross-sectional display panel image and a two-dimensional tomographic display panel image based on the digital signal, and generates a three-dimensional display panel image for each layer of the display panel based on the two-dimensional tomographic display panel image.

16. The system according to claim 12, wherein the foreign substance detecting part comprises:
a foreign substance size calculating part which detects the foreign substance by comparing the image of the display panel with a previously stored reference image and calculates a size of the foreign substance through location coordinates of the foreign substance from the image of the display panel; and
a foreign substance deciding part which determines a defect is present when the size of the foreign substance calculated through the foreign substance detecting part exceeds the predetermined reference size of the foreign substance.

17. The system according to claim 12, wherein the display panel to be inspected is a touchscreen panel or a display device to which the touchscreen panel is applied.

18. A non-destructive inspection method to inspect a display panel, comprising:
dividing light emitted from a light source and irradiating the divided light to a reference part and a sample part using a non-destructive inspection apparatus;
phase-scanning light incident from an optical coupler and reflecting the light using the reference part;
irradiating light incident from the optical coupler to a display panel to be inspected, and scanning and reflecting the light reflected from the display panel using the sample part;
moving a position of the display panel up and down according to the scanning of the light reflected from the display panel so that the display panel is located at a predetermined scan area, thereby enabling automatic focusing on the display panel to be inspected,
generating a one-dimensional cross-sectional display panel image based on light incident from the reference part and the sample part, and identifying existence of a foreign substance based on a refractive index according to each material appearing on the one-dimensional cross-sectional display panel image;

generating a one-dimensional display panel image based on light incident from the reference part and the sample part;

generating a two-dimensional display panel image based on the one-dimensional display panel image; and generating a three-dimensional display panel image based on the two-dimensional display panel image.

19. The method according to claim 18, further comprising primarily determining a foreign substance estimation area located on a surface of the display panel, before the dividing of light and the irradiating of the divided light to the reference part and the sample part.

20. The method according to claim 19, wherein, in the irradiating of light to a display panel to be inspected, and the scanning and reflecting of the light reflected from the display panel, when irradiating the light to the display panel, the light is irradiated along a predetermined observation range on the basis of the foreign substance estimation area.

21. The method according to claim 20, wherein, when the light is irradiated along the predetermined observation range, the light is irradiated to a single point.

22. The method according to claim 19, further comprising:

calculating a size of a foreign substance from the two-dimensional display panel image; and deciding that a defect is present when the calculated size of the foreign substance exceeds a predetermined size of the foreign substance.

23. A non-transitory computer-readable recording medium storing a program to implement the method of claim 18.

* * * * *